United States Patent

Lorenz

Patent Number: 6,093,855
Date of Patent: Jul. 25, 2000

[54] SEPARATION OF THE DIVINYL ETHER OF DIETHYLENE GLYCOL OR TRIETHYLENE GLYCOL FROM THE MONOVINYL ETHER OF THE CORRESPONDING OLIOGETHYLENE GLYCOL

[75] Inventor: Rudolf Erich Lorenz, Ludwigshafen, Germany

[73] Assignee: BASF Aktiengesellschaft, Ludwigshafen, Germany

[21] Appl. No.: 09/159,085

[22] Filed: Sep. 23, 1998

[30] Foreign Application Priority Data

Sep. 30, 1997 [DE] Germany ............... 197 43 144

[51] Int. Cl.⁷ .................................................. C07C 43/16
[52] U.S. Cl. ................. 568/621; 568/619; 568/616; 203/36; 203/37; 203/50; 203/63
[58] Field of Search .................. 568/616, 619, 568/621; 203/63, 50, 36, 37

[56] References Cited

U.S. PATENT DOCUMENTS 1,959,927  5/1934  Reppe ........................ 260/127
3,492,358  1/1970  Gurgiolo et al. ............ 568/621
5,723,685  3/1998  Heider et al. ............... 586/688

FOREIGN PATENT DOCUMENTS 10045653  2/1998  Japan .

OTHER PUBLICATIONS

Yoshiyuki, *Pat. Abst. of Japan*, vol. 12, No. 270 (C–515), Jul. 27, 1988 (English abstract of JP 63 051344, Mar. 4, 1988).

*Primary Examiner*—Johann Richter
*Assistant Examiner*—Rosalynd Keys
*Attorney, Agent, or Firm*—Keil & Weinkauf

[57] ABSTRACT

The divinyl ethers of diethylene glycol or triethylene glycol are separated from the monovinyl ether of the corresponding oligoethylene glycol by distillation, a metal hydroxide being added to the vinyl ether mixture.

2 Claims, No Drawings

SEPARATION OF THE DIVINYL ETHER OF DIETHYLENE GLYCOL OR TRIETHYLENE GLYCOL FROM THE MONOVINYL ETHER OF THE CORRESPONDING OLIOGETHYLENE GLYCOL

The present invention relates to a process for separating by distillation the divinyl ether of diethylene glycol or triethylene glycol from the monovinyl ether of the corresponding oligoethylene glycol.

Divinyl ethers of diols are useful crosslinkers which are used to increase the internal strength of polymers prepared by free-radical-initiated polymerization of compounds (monomers) having at least one ethylenically unsaturated group.

The most important industrial method for preparing vinyl ethers is addition of alcohol to acetylene in the presence of catalytically active alkali metal alkoxide in the homogeneous liquid phase. Vinylation is generally at from 150 to 180° C. Furthermore, the reaction generally takes place at superatmospheric pressure.

When divinyl ethers are prepared, the alcohol used is a diol. Vinylation then takes place in two successive steps. Firstly, essentially only the monovinyl ether of the diol is formed, which then reacts further to form the divinyl ether.

If the diol used is diethylene glycol or triethylene glycol, the reaction to form the corresponding divinyl ether is generally terminated before divinyl ether has been formed quantitatively. The reason for this is an increase in viscosity accompanying the reaction, which makes it increasingly more difficult to force in acetylene substantially.

Usually, therefore, in the preparation of the divinyl ether of diethylene glycol or triethylene glycol, a reaction mixture is produced which, in addition to a predominant amount of divinyl ether, can still comprise up to 5% by weight, based on the amount of mixture, of the corresponding monovinyl ether. However, if the intended use of the divinyl ethers is as crosslinker, a monovinyl ether content interferes, for which reason separating the divinyl ether from the monovinyl ether is indicated. To achieve this separation task, in a simple manner work-up by rectification of the reaction mixture at reduced pressure is available. The latter is required on account of the high boiling point of the divinyl ether of diethylene glycol and triethylene glycol. Remarkably, the boiling point of the divinyl ether of diethylene glycol and triethylene glycol is below the boiling point of each corresponding monoether, which is thought to be due to the fact that the monovinyl ether is still capable of forming hydrogen bonds.

Since the difference in boiling points between monovinyl ether and divinyl ether in the two abovementioned cases is not very pronounced (b.p. of diethylene glycol monovinyl ether=90° C. at 6 mbar; b.p. of diethylene glycol divinyl ether=89° C. at 13 mbar), it was assumed that separation by rectification would require a high-efficiency column. However, surprisingly, it has been found that the content of monovinyl ether of diethylene glycol or triethylene glycol in the divinyl ether of the corresponding diol produced as distillate at the column top could not be substantially decreased below 1% by weight, based on the distillate, regardless of the reflux ratio and the number of theoretical plates.

This is concluded to be due to the fact that the divinyl ether and the monovinyl ether evidently form an azeotrope.

It is an object of the present invention to provide a process for separating by distillation the divinyl ether of diethylene glycol or triethylene glycol from small amounts of monovinyl ether of the corresponding oligoethylene glycol. We have found that this object is achieved, against the background of the abovementioned finding, by adding a metal hydroxide to the mixture to be separated by distillation before the separation. Preferably, an alkali metal hydroxide and/or an alkaline earth metal hydroxide is added. Particular preference is given to addition of potassium hydroxide and/or sodium hydroxide. Obviously, however, calcium hydroxide can also be used.

Triethylene glycol divinyl ether or diethylene glycol divinyl ether can therefore be prepared by vinylating with acetylene the corresponding oligoethylene glycol in the presence of alkali metal alkoxide of the corresponding diol (based on the oligoethylene glycol generally up to 3% by weight) (preferably at from 150 to 180° C. and at superatmospheric pressure of up to 20 bar), until the remaining content of monovinyl ether, based on the reaction mixture, is $\geq 0.5\%$ by weight and $\leq 5\%$ by weight. Thereafter, either metal hydroxide can be added immediately to the reaction mixture and the divinyl ether can then be separated off by distillation and/or rectification from the reaction mixture, from monovinyl ether still present, or, firstly the volatile constituents, which essentially consist of divinyl ether and monovinyl ether, are separated off from the reaction mixture by distillation, and metal hydroxide is added to the resulting distillate in order then to separate off the divinyl ether from the monovinyl ether by distillation and/or rectification.

The amount of metal hydroxide to be added is generally according to the invention such that it would be able to neutralize about 1.2 times the molar amount of the resulting monovinyl ether. Advantageously, the metal hydroxide is added according to the invention as aqueous solution.

It is of importance that the process according to the invention need not necessarily be carried out as a rectification, but can also be carried out as simple distillation (only one theoretical plate), eg. in a Sambay thin-film evaporator.

According to the invention, divinyl ethers of triethylene glycol or diethylene glycol are thus obtainable in a simple manner with a content of monovinyl ether of the corresponding oligoethylene glycol$\leq 0.1\%$ by weight.

EXAMPLES

| A) 200 g of a mixture consisting of | |
|---|---|
| 197 g | of triethylene glycol divinyl ether |
| 2.1 g | of triethylene glycol monovinyl ether and |
| 1 g | of by-products due to the preparation method | were admixed with 1.5 g of a 50% strength by weight aqueous potassium hydroxide solution. The mixture was then subjected to a simple distillation at an operating pressure of 6 mbar until no more distillate passed overhead (boiling point$\approx$105° C.)

The distillate obtained had the following composition:

| | |
|---|---|
| 99.66% by weight | of triethylene glycol divinyl ether |
| 0.1% by weight | of triethylene glycol monovinyl ether |
| 0.24% by weight | of other compounds. |

The distillation residue was about 6 g. It consisted of a highly viscous solution which comprised up to 24% by weight of triethylene glycol monovinyl ether.

B) A mixture whose composition corresponded to that of the mixture in A) was rectified in a packed column of the following type (21 theoretical plates). The column diameter was 1.38 m. The packing consisted of 3S Pall rings (stainless steel) from Raschig. The total bed height of the packing was 14.5 m (distributed on 5 packed beds). The pressure at the column top was set to 6 mbar. The bottom temperature was from 140 to 150° C. The mixture to be separated by rectification was fed to the column.

The condensate produced at the column top had the following composition:

| | |
|---|---|
| 99% by weight | of triethylene glycol divinyl ether and |
| 1% by weight | of triethylene glycol monovinyl ether. |

A subsequent rectification of the condensate in a corresponding column and under corresponding conditions gave no further separation.

We claim:

1. A process for separating by distillation and/or rectification the divinyl ether of diethylene glycol or triethylene glycol from a mixture which consists of at least 95% by weight of one of the two abovementioned divinyl ethers and of up to 5% by weight of the monovinyl ether of the corresponding oligoethylene glycol, which comprises adding a metal hydroxide to the mixture before and/or during the separation by distillation and/or rectification.

2. A process for preparing the divinyl ether of diethylene glycol or triethylene glycol by vinylation of diethylene glycol or triethylene glycol with acetylene in the liquid phase and in the presence of alkali metal alkoxide of the corresponding oligoethylene glycol until the remaining content of monovinyl ether, based on the reaction mixture, is $\geq 0.5\%$ by weight and $\leq 5\%$ by weight and subsequent separation by distillation and/or rectification of the divinyl ether from the reaction mixture, which comprises adding a metal hydroxide to the reaction mixture, which comprises $\geq 0.5\%$ by weight and $\leq 5\%$ by weight of monovinyl ether, before and/or during the separation by distillation and/or rectification.

* * * * *